United States Patent
Wegener et al.

(10) Patent No.: US 8,354,252 B2
(45) Date of Patent: Jan. 15, 2013

(54) LABELED REACTANTS AND THEIR USES

(75) Inventors: Jeffrey Wegener, Cupertino, CA (US); Jonas Korlach, Newark, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 61 days.

(21) Appl. No.: 13/115,288

(22) Filed: May 25, 2011

(65) Prior Publication Data

US 2011/0311964 A1 Dec. 22, 2011

Related U.S. Application Data

(63) Continuation of application No. 12/403,090, filed on Mar. 12, 2009, now Pat. No. 7,968,702.

(60) Provisional application No. 61/069,247, filed on Mar. 13, 2008.

(51) Int. Cl.
- *C12P 19/34* (2006.01)
- *C12Q 1/68* (2006.01)
- *C07H 21/00* (2006.01)
- *C07H 21/02* (2006.01)

(52) U.S. Cl. ...... 435/91.1; 435/6.1; 536/23.1; 536/24.3; 536/24.33; 536/26.6

(58) Field of Classification Search .......... 435/6.1, 435/91.1; 536/23.1, 24.3, 24.33, 26.6
See application file for complete search history.

(56) References Cited

U.S. PATENT DOCUMENTS

| | | | |
|---|---|---|---|
| 5,332,567 A | 7/1994 | Goldenberg | |
| 6,544,797 B1 | 4/2003 | Buechler et al. | |
| 6,664,079 B2 * | 12/2003 | Ju et al. | 435/91.1 |
| 7,052,839 B2 | 5/2006 | Nelson et al. | |
| 7,170,050 B2 | 1/2007 | Turner et al. | |
| 7,223,541 B2 | 5/2007 | Fuller et al. | |
| 7,993,891 B2 * | 8/2011 | Roitman et al. | 435/174 |
| 2003/0124576 A1 | 7/2003 | Kumar et al. | |
| 2004/0023413 A1 | 2/2004 | Opalsky | |
| 2005/0244863 A1 | 11/2005 | Mir | |
| 2007/0036511 A1 | 2/2007 | Lundquist et al. | |
| 2007/0072196 A1 | 3/2007 | Xu et al. | |
| 2007/0161017 A1 | 7/2007 | Eid et al. | |
| 2008/0026380 A1 * | 1/2008 | Siddiqi et al. | 435/6 |
| 2008/0277595 A1 | 11/2008 | Lundquist et al. | |
| 2010/0092957 A1 | 4/2010 | Zhao et al. | |

FOREIGN PATENT DOCUMENTS

WO 2007075873 7/2007

(Continued)

OTHER PUBLICATIONS

Halpin, D.R. et al., "DNA display III. Solid-phase organic synthesis on unprotected DNA" PLOS Biology (2004) 2(7):1031-1038.

(Continued)

*Primary Examiner* — Jezia Riley
(74) *Attorney, Agent, or Firm* — Robert H. Reamey; Matthew B. Murphy

(57) ABSTRACT

Labeled reactant compositions, and particularly labeled nucleic acid reaction compositions, that include structural components that maintain potentially damaging labeling components sufficiently distal from the reactant portion of the molecule such that damaging effects of the label group on other reaction components, such as enzymes, are reduced, minimized and/or eliminated.

10 Claims, 6 Drawing Sheets

FOREIGN PATENT DOCUMENTS

| | | |
|---|---|---|
| WO | 2007075987 | 7/2007 |
| WO | 2007076057 | 7/2007 |
| WO | 2007095119 | 8/2007 |

OTHER PUBLICATIONS

International Search Report and Written Opinion dated Aug. 25, 2009 for related case PCT/US2009/001609.

Fagan, A. et al., "Rigid Cyanine Dye Nucleic Acid Labels" Chem Comm Royal Soc of Chem (2008) pp. 2004-2006.

Knorre D.G. et al., "General Method for the Synthesis of ATP Gamma-Derivatives" FEBS Lett (1976) 70(1):105-108.

Kumar, S. et al., "Terminal Phosphate Labeled Nucleotides: Synthesis, Applications, and Linker Effect on Incorporation by DNA Polymerases" Nucleosides, Nucleotides, and Nucleic Acid (2005) 24:401-408.

Schuler, B. et al., "Polyprolin and the 'spectroscopic ruler' revisited with single-molecule fluorescence" PNAS (2005) 102(8):2754-2759.

\* cited by examiner ical processes, researchers are constantly looking for new and better ways to eavesdrop on both the individual reactions that make up complex biological systems, as well as observe the operation of those systems as a whole. In doing so, researchers have developed methods, systems and compositions that employ artificially labeled molecules as model constituents for those reactions and systems. Observation of the model molecules is rendered facile by the presence of the labeling group. Such labels include radioactive compounds or radiolabels, chromophoric labels that absorb and/or reflect light of different wavelengths to provide colored indications of an event, chemiluminescent labels that can spontaneously emit light in response to a particular chemical event, fluorescent labels that emit light in response to excitation by light of a different wavelength, and reporter system labels, that provide an exogenous, assayable activity or property to indicate the presence, absence or change in the model molecule. Such reporter labels often include exogenous enzymes, binding molecules or the like that are capable of being identified and even quantified.

LABELED REACTANTS AND THEIR USES

CROSS-REFERENCE TO RELATED APPLICATIONS

This application is a continuation of U.S. patent application Ser. No. 12/403,090, filed Mar. 12, 2009, which claims benefit of U.S. Provisional Patent Application No. 61/069,247, filed Mar. 13, 2008, the full disclosures of which are hereby incorporated by reference in their entirety for all purposes.

STATEMENT REGARDING FEDERALLY SPONSORED RESEARCH

Not Applicable.

BACKGROUND OF THE INVENTION

In the analysis of biological processes, researchers are constantly looking for new and better ways to eavesdrop on both the individual reactions that make up complex biological systems, as well as observe the operation of those systems as a whole. In doing so, researchers have developed methods, systems and compositions that employ artificially labeled molecules as model constituents for those reactions and systems. Observation of the model molecules is rendered facile by the presence of the labeling group. Such labels include radioactive compounds or radiolabels, chromophoric labels that absorb and/or reflect light of different wavelengths to provide colored indications of an event, chemiluminescent labels that can spontaneously emit light in response to a particular chemical event, fluorescent labels that emit light in response to excitation by light of a different wavelength, and reporter system labels, that provide an exogenous, assayable activity or property to indicate the presence, absence or change in the model molecule. Such reporter labels often include exogenous enzymes, binding molecules or the like that are capable of being identified and even quantified.

In attaching label groups to different model reaction constituents, one runs the risk that the presence of the label will adversely impact the reaction being observed. For example, large hydrophobic labeling groups can present issues of steric interference with the progress of the reaction of interest by blocking or not properly interacting with the other reaction constituents. Likewise, labeling components that impact the chemical properties of the model compound or the reaction environment can similarly adversely impact reaction conditions. In other cases, the properties of the label itself may adversely affect the reaction components. For example, the presence of fluorescent molecules in close proximity to enzymatic reaction components can lead to decay in the level of enzyme activity through photo-chemically induced reaction intermediates or other impacts.

Accordingly, it would be desirable to provide reaction components that provide remedies to some of the issues created by the incorporation of labeling groups on reaction constituents. The present invention provides these and other solutions.

BRIEF SUMMARY OF THE INVENTION

The invention generally relates to labeled compounds that comprise linker groups coupling the labeling moiety to the reactive portion of the compound such that the labeling group is maintained a sufficient distance away from the reactive portion that potential negative impacts of the label moiety on the reactive portion or other compounds, enzymes or other reactants that react with the reactive portion, are avoided, reduced or otherwise mitigated. In one aspect, the invention provides a labeled reactant composition, that comprises a reactant component, a label component, and a linker component coupling the label component to the reactant component. The linker component maintains the label component at a functional distance from the reactant component of at least 2 nm.

In another aspect, the invention provides a composition, comprising an enzyme, and a substrate for the enzyme, the substrate comprising a reactant component, a label component and a linker component. The linker component maintains the label component at a functional distance away from the reactant component that a negative impact of the label component on the enzyme is reduced by at least 20%.

In a further aspect, the invention provides a method of monitoring an enzyme reaction. The method generally comprises providing a reaction mixture comprising the enzyme and at least a first reactant composition, the reactant composition comprising a compound having a reactant component, a fluorescent label component, and a linker component joining the reactant component to the label component, wherein the linker component maintains the label component at a functional distance away from the reactant component that a negative impact of the label component on the enzyme is reduced by at least 20%. The reaction mixture is then illuminated to excite the fluorescent label component, and a fluorescent signal from the reaction mixture characteristic of the enzyme reaction is detected.

The invention also provides methods of monitoring nucleic acid synthesis reactions. The methods comprise contacting a polymerase/template/primer complex with a fluorescently labeled nucleotide or nucleotide analog having a nucleotide or nucleotide analog component, a fluorescent label component, and a linker component joining the nucleotide or nucleotide analog component to the label component, wherein the linker component maintains the label component at a functional distance away from the nucleotide or nucleotide analog component that a negative impact of the label component on the enzyme is reduced by at least 20%. A characteristic signal from the fluorescent dye is then detected that is indicative of incorporation of the nucleotide or nucleotide analog into a primer extension reaction.

DETAILED DESCRIPTION OF THE INVENTION

I. General

Figure 1:
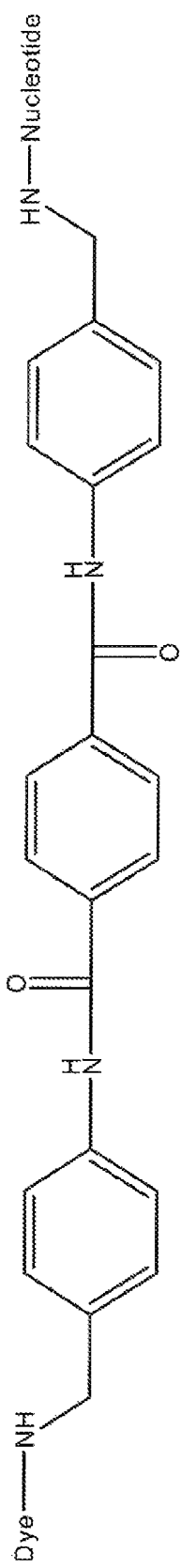
FIG. 1 schematically illustrates one exemplary aromatic linker for use in the present invention.

The present invention is directed to labeled reactants and their uses that have improved characteristics for use in analytical operations. In particular, provided are compositions and methods of using such compositions, in which the label component of the molecule, while still attached to the reactant component of the molecule, is nonetheless provided sufficiently distal to that reactant component to minimize potential adverse effects of that labeling component on the reaction of interest. Specifically, the linkage between the labeling group and the reactant group is configured to maintain sufficient distance between the two, such that negative or adverse impacts of the labeling group on the reaction of the reactant with other components is minimized. Of particular interest is the use of linker moieties that provide for the maintenance of fluorescent labeling groups outside of the active site of the enzyme(s) that are involved in the reaction of interest, and preferably, sufficiently distant from key portions of enzymes that are reacting with the molecules to which such labels are attached, so that any adverse or negative impacts of the labeling group on the enzyme or other reactants interacting with the enzyme, are reduced, minimized or eliminated.

For purposes of description, the reactant that bears the labeling group will be referred to herein as the first reactant, which is comprised of a label portion and a reactant portion. The reactant portion denotes the portion of the first reactant that serves as the reactant in the reaction of interest, with or without the label group. For example, in nucleic acid reactions utilizing fluorescently labeled nucleotide analogs as the first reactant, the label portion that includes the fluorescent dye component is connected to a nucleotide or nucleotide analog that forms the reactant portion.

Typically, the linker configurations of the present invention provide for a linkage of sufficient length and sufficient structure or rigidity to maintain the desired distance between the label portion and the reactant portion of the first reactant during a given reaction, such that adverse impacts of the label portion on either of the reactant portion or other reaction components which react with the reactant portion are reduced, minimized or eliminated. In particular, while actual linker length is one important factor in the maintenance of the label at a desired distance, functional length, e.g., the actual distance maintained between the label portion and the reactant portion, is believed to be the key influence, in that most adverse effects are believed to based upon relative proximity between the labels and the other reactants which suffer adverse impacts.

In a first aspect, the maintenance of sufficient distance between the label portion and the reactant portion of the first reactant may be characterized as a function of the desired reduction in a given adverse impact, as compared to similar molecules in which the label group is within a distance of about 1 nm of the reactant group. By way of example, in a nucleic acid polymerase mediated primer extension reaction that uses labeled nucleotide analogs where the label group is coupled to the nucleotide portion by a relatively short hexyl linker, e.g., a linkage that depending upon the level of coiling, can be from less than 1 nm to about 2 nm in a fully stretched configuration, it has been observed that when the reaction is carried out under excitation illumination, that within the first minute of the reaction, the polymerase activity can be depleted by as much as 50%, depending upon the illumination conditions, reaction conditions, and fluorescent materials present.

As noted above, in this context, the compositions of the present invention typically provide sufficient distance between the label component and the reactant component as to reduce such photo-induced decrease in enzymatic activity over that which occurs where the fluorescent label component is closer to the reactant component, i.e., nucleotide, such as is the case where a hexyl linker is employed.

In accordance with the present invention, substitution of the linkages described herein, will yield a 20% reduction in the amount of the depletion over the same time period as compared to a linkage that has the shorter functional length (e.g., less than 2 nm), preferably a 50% reduction in that depletion, more preferably at least a 90% or even at least a 95% reduction in that depletion over the same time period. With respect to a 90% reduction, for example, if the normal depletion in activity is 50% using a labeled molecule with a 1 to 2 nm linkage, then the corrected depletion would be no more than 5% (a 90% reduction in the 50% depletion, meaning one would regain the 45% of activity that would otherwise be lost).

In another aspect, the reactants of the invention are characterized by the specific distances provided between the reactant portion and the label portion. Because of differences in the relative flexibility of different linkages, such distances are generally stated in terms of an operating or functional distances, e.g., the average maintained distance between label group and reactive group. In the case of linear linkages, such distances may be provided using polymers or other linear structures that have persistence lengths of at least the desired distances. Alternatively, some linkages may provide a spatial separation based upon the volume of the linkage, e.g., PEG linkers that may exist as a random coil that provides a consistent spatial separation between the label group and the reactive group.

While precise distances or separation may be varied for different reaction systems to obtain optimal results, in many cases it will be desirable to provide a linkage that maintains fluorescent label groups at least 2 nm from the reactant portion of the first reactant, and in some cases at least 5 nm from the reactant portion of the first reactant or even at least 10 nm from the reactant portion.

A number of linkers may be employed that will provide the desired separation between label and reactant portion of the molecule. For example, alkyl linkers may be used that provide a useful distance between the reactant group and the dye group. For example, longer amino-alkyl linkers, e.g., amino-hexyl linkers, have been used to provide dye attachment to nucleotide analogs, and are generally sufficiently rigid to maintain such distances.

In preferred aspects, however, providing linkers with desired functional lengths typically involves the use of more rigid chemical structures in such linkers. Typically, such rigid structures include laterally rigid chemical groups, e.g., ring structures such as aromatic compounds, multiple chemical bonds between adjacent groups, e.g., double or triple bonds, in order to prevent rotation of groups relative to each other, and the consequent flexibility that imparts to the overall linker. Alternatively or additionally, secondary chemical structures may be used to impart rigidity, including, for example helical structures, sheet structures, and the like, as well as structures that employ cooperative molecules in providing rigidity, e.g., complementary molecular structures.

As noted, some linkers according to the invention derive rigidity through the internal chemical structure of the linker molecules. For example, linker molecules may derive their rigidity through a reduction in the number of single bonds that could yield points of rotation, and thus, flexibility in the linker. As such, the linkers will typically comprise double bonds, triple bonds or ring structures, which will provide the increased rigidity. Examples of double and/or triple bonded linker structures include, for example, conjugated alkynes, conjugated alkenes, aryl alkynes, and the like. While illustrated as polymeric structures of repeating monomeric subunits, it will be appreciated that the linkers of the invention may comprise mixed polymers of differing monomeric subunits.

Figure 2:
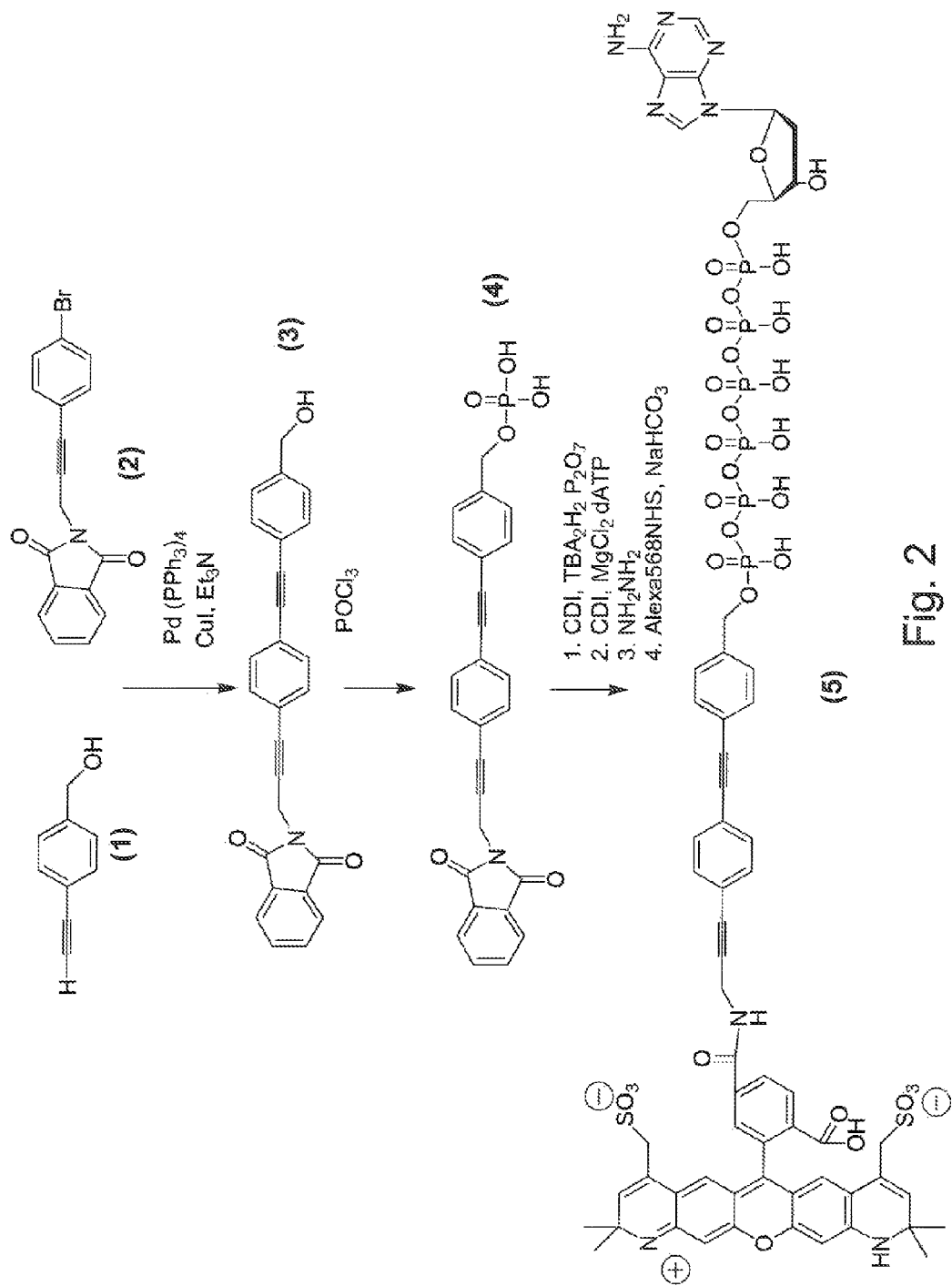
FIG. 2 schematically illustrates the structure and an exemplary synthesis of aromatic linkers.

Linkers that comprise ring or aromatic structures can include, for example aryl alkynes and aryl amides. One exemplary aromatic linker is illustrated in FIG. 1, which shows an aryl alkyne, linking a dye group to a nucleotide or nucleotide analog. Although illustrated as a dimer, it will be appreciated that the length of the linker is readily increased by the addition of monomers in the synthesis process that is schematically illustrated in FIG. 2. As shown, Heck coupling of the aryl bromide (2) and aryl alkyne (1) is followed by phosphorylation of the resulting alcohol (3). The phosphate of the resulting phosphorylated compound (4) is coupled to the terminal phosphate of a nucleotide by carbonyldiimidizole activation, followed by deprotection of the amine. The dye moiety is then added using standard NHS chemistry to yield the dye labeled nucleoside hexaphosphate analog (5).

Figure 3:
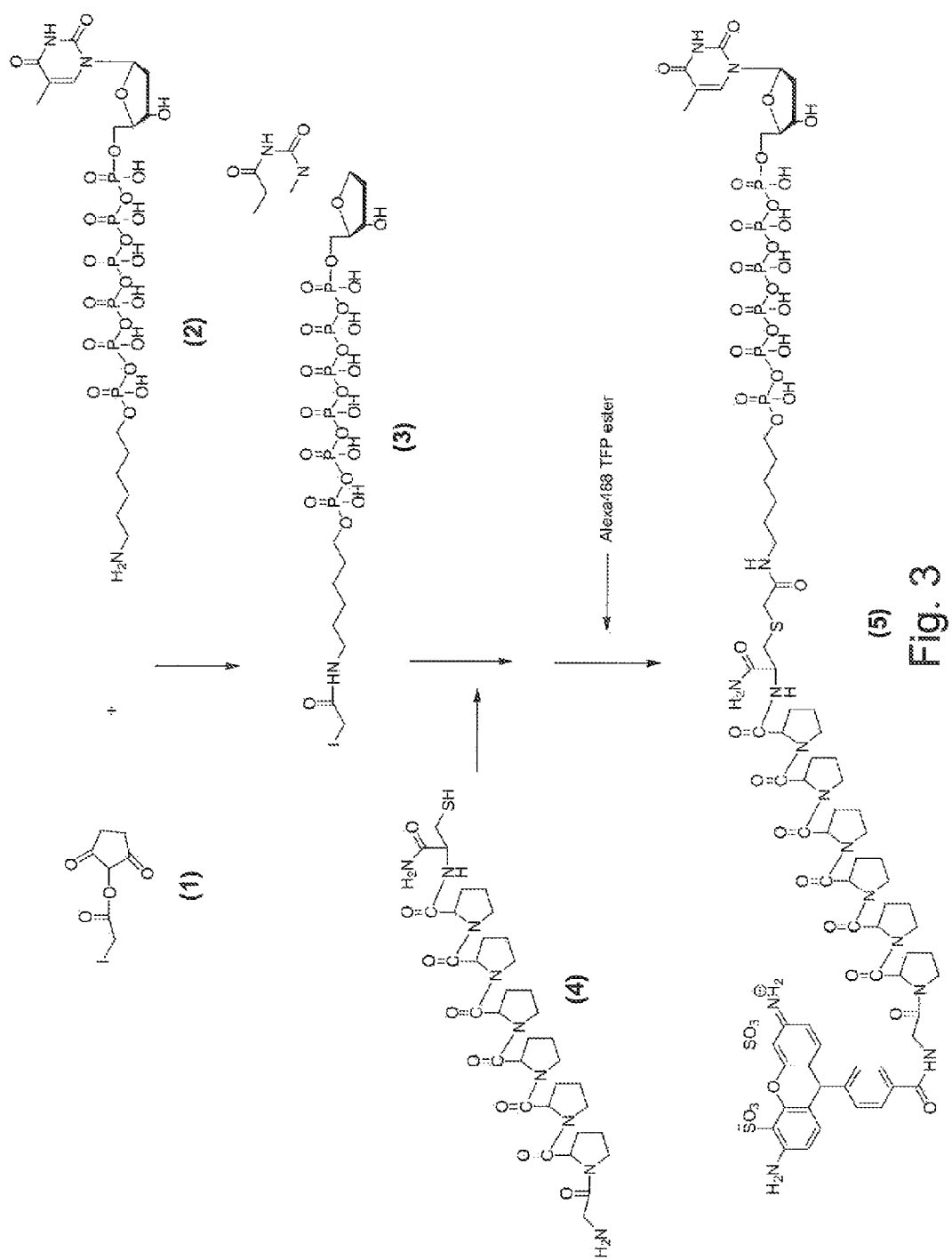
FIG. 3 schematically illustrates a labeled nucleotide analog comprising an oligoproline linker in accordance with the invention.

Other examples of the linkers of the invention include oligopeptide linkers, and in particular, oligoproline linkers that also include ring structures within their structure. Oligoproline linkers will typically have the structure shown in FIG. 3. An exemplary strategy for linking dye groups to nucleotides or nucleotide analogs is also illustrated in FIG. 3. In particular, a NHS activated iodoacetamide (1) is coupled to an amino-linker nucleotide (2) to yield the nucleotide analog (3). This is coupled to the thiol group of the peptide Gly-(Pro)$_6$-Cys peptide (4). The dye group is then coupled to amino terminus on the glycine residue as the TFP ester to form the dye labeled nucleotide analog (5).

The linkers used in the context of the invention may additionally or alternatively derive rigidity from secondary, tertiary or even quaternary structures. For example, in some cases, polypeptide linkers may be employed that have helical or other rigid structures. Such polypeptides may be comprised of rigid monomers, e.g., as in the oligoproline linkers described previously, which derive rigidity both from their primary structure, as well as from their helical secondary structures, or may be comprised of other amino acids or amino acid combinations or sequences that impart rigid secondary or tertiary structures, such as helices, fibrils, sheets, or the like. By way of example, polypeptide fragments of structured rigid proteins, such as fibrin, collagen, tubulin, and the like may be employed as rigid linker molecules.

In a related aspect, double stranded nucleic acids can be used to provide both the requisite length and rigidity as a linker. Similarly, related structures, such as double stranded peptide nucleic acids (PNAs), or DNA/PNA hybrid molecules may be employed as the linkers (See, e.g., FIG. 3, below). By way of illustration, the persistence length of double stranded nucleic acids, i.e., the length up to which the structure behaves more rod-like than rope-like, is approximately 50 nm, allowing for facile construction of rigid linkers up to and even beyond this length.

II. Nucleotide Analogs and Polymerases

In particularly preferred aspects, the compounds of the invention comprise fluorescently labeled nucleotides or nucleotide analogs that are used in enzymatic reactions, and particularly polymerization reactions in which the fluorescent label is excited during the synthesis process. In particular, fluorescently labeled nucleotide analogs have been shown to negatively impact the activity of nucleic acid polymerases, when the reaction between the polymerase and the analog is carried out under conditions that excite the fluorescent label, i.e., under excitation illumination. In particular, a fluorescent label group or fluorophore, excited by exposure to electromagnetic radiation at an excitation wavelength can transition into a triplet state. Subsequent relaxation of the triplet state fluorophore can then lead to generation of reactive oxygen species. Without being bound to a particular theory of operation, it is believed that generation of these reactive species within or sufficiently proximal to the active site of enzymes such as polymerases, can lead to damage to one or both of the fluorophore and/or the enzyme processing the fluorescently labeled reactant.

Previous approaches have sought to mitigate the impacts of these species by including agents within the overall reaction that mitigate the problematic issues, e.g., oxygen scavenging agents (See, e.g., Published U.S. Patent Application No: 2007-0161017, which is incorporated herein by reference in its entirety for all purposes). In contrast, the present invention, instead of or in addition to providing mitigating agents within the reaction mixture, provides the fluorescent labeling group away from key components of the enzyme, such as the active site. As noted above, this is accomplished by providing the compounds of the invention with a linker molecule between the nucleotide or nucleotide analog and the label group, which linker group is sufficiently long and possessing of sufficient structure to maintain the label in a position away from the enzyme, or key portions thereof. As such, the linker molecules will typically be longer than a threshold distance and will be sufficiently rigid to maintain the fluorophore at a sufficient distance during a reaction, as set forth above. In the context of polymerase mediated synthesis reactions using excited fluorescently labeled nucleotides or analogs thereof, it will be appreciated that the sufficient distance may be characterized as set forth above, e.g., based upon a prescribed reduction in the level of depletion of polymerase activity as compared to nucleotides where the fluorescent group is within less than 2 nm.

The nucleotide analogs of the invention may comprise any of the biologically relevant nucleotides or deoxynucleotides or analogs thereof including ribonuclotides and deoxyribonucleotides or analogs thereof. Typically, such nucleotides or analogs include, adenosine, thymidine, guanosine, cytidine, uracil, and analogs of these. The analogs may comprise nucleoside triphosphates, or in preferred aspects may include additional phosphate groups, e.g., tetraphosphates, pentaphosphates, hexaphosphates, heptaphosphates, or greater. Examples of some of these analogs are described, for example, in Published U.S. Patent Application Nos. 2003-0124576 and 2007-0072196, as well as U.S. Pat. Nos. 7,223, 541 and 7,052,839, the full disclosures of which are incorporated herein by reference in their entirety for al purposes.

The compounds of the invention will typically include any of a variety of fluorophores as the labeling portion, including, for example, fluorescein based dyes, rhodamine based dyes, cyanine based dyes (Cy3, Cy5, and others, available from GE Healthcare). Other fluorophores that are readily commercially available include those available from Invitrogen/Molecular Probes (Carlsbad, Calif.), such as the Alexa® dyes, e.g., Alexa 488, 555, 568 and 660.

As noted previously, the linkage between the labeling portion and the reactant portion of the first reactant, e.g., a fluorescent dye and a nucleotide analog, is configured to provide sufficient linker length and structure as to maintain the label a sufficient distance from the reactant portion such that negative impacts of the label portion on the reactant portion, or those reaction components that interact with the reactant portion, are minimized or avoided. In the context of nucleic acid sequencing that employs real-time detection of the interaction of labeled nucleotides with polymerase enzymes, one impact that is sought to be avoided, is the impact of the excited fluorophore, or its by-products, on the activity of a polymerase enzyme interacting with the nucleotide. In particular, and as noted above, it has been found that excitation of fluorescently labeled nucleotides as they interact with nucleic acid polymerase molecules, can yield a substantial reduction in the activity of those polymerase molecules over time (See, Published U.S. Patent Application No. 2007-0161017, which is incorporated herein by reference in its entirety for all purposes). Again, without being bound to a particular theory of operation, it is believed that by-products of the fluorescent excitation reaction cause damage to the portions of the polymerase that are proximal to the fluorophore, e.g., the active site.

As noted previously, the linkers of the invention serve to distance the fluorophore from the reactant portion, such that the negative impact is reduced or avoided. As noted previously, the reduction in the negative impact will be at least 10%, more preferably, at least 20%, and still more preferably, at least a 50% reduction in the negative impact, as compared to linkers that maintain the fluorophore within 2 nm of the reactant portion of the molecule. In the context of a reduction in photodamaging effects, therefor, it will be appreciated that the analogs of the invention, e.g., including the linkers described herein, will result in a decrease in the activity reduction of at least 10%, more preferably 20% and still more preferably, at least 50%, as compared to the reduction in activity when using a similarly labeled nucleotide analog having a linkage with a persistence length less than 2 nm.

While linker length is typically a function of providing a sufficient number of monomers or other linkage units in the linker molecule, providing sufficient structure typically involves adjusting the nature of those monomeric units so as to provide a structurally more rigid linker.

As noted above, in certain preferred aspects, a nucleic acid linker that comprises a double stranded portion to impart rigidity is used as the linker group between the reactant component, e.g., the nucleotide or nucleotide analog, and the label component, e.g., the fluorophore. Such double stranded nucleic acids may comprise distinct but complementary nucleic acid strands that are hybridized together, where one or both strands bear a label component. Alternatively, the nucleic acid linker may comprise a single molecule with complementary portions, such that the molecule self hybridizes to form a hairpin loop structure, where the label component is provided at a point on the loop, distal to the reactant portion. The use of nucleic acid linker structures provides advantages of ease of synthesis of the labeled linker, using conventional DNA synthesis and dye coupling techniques, and resultant control of linker length, e.g., approximately 0.3 nm of distance imparted for each added monomer in the linker portion. Consequently, one can easily adjust the length of the linker to accommodate more or less sensitive reaction systems. Additionally, the ability to adjust the rigidity of the linker, in real time provides interesting reaction control elements, e.g., by adjusting the integrity of the hairpin structure by modifying the hybridization conditions for the linker, e.g., adjusting salt, temperature, or the like. These linkers are also readily coupled to nucleotide analogs, whether coupled through groups on the nucleobase, the ribosyl moiety, or through one of the phosphate groups (e.g., alpha, beta, gamma, or others in the case of tetra, penta, or hexa phosphate analogs, or others).

Figure 4A:
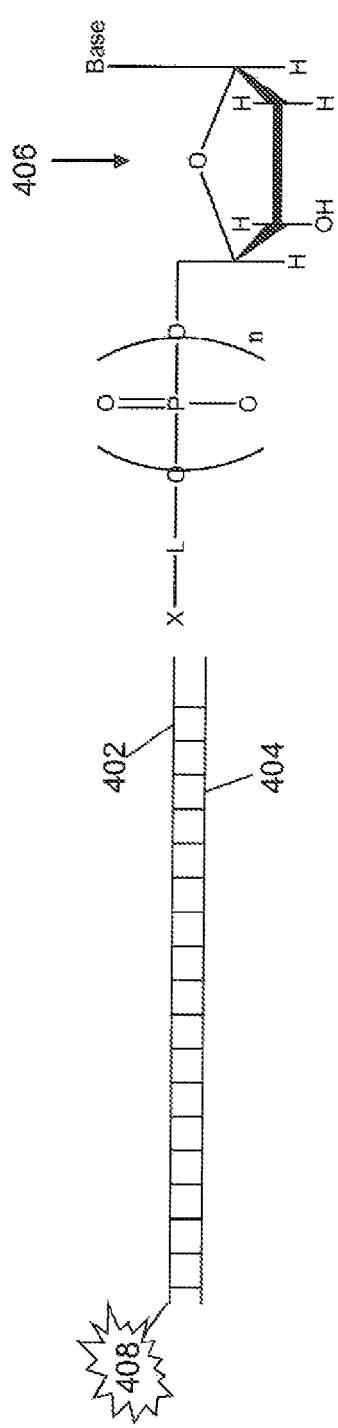
FIG. 4 schematically illustrates alternative double stranded nucleic acid linkers of the invention.
Figure 4B:
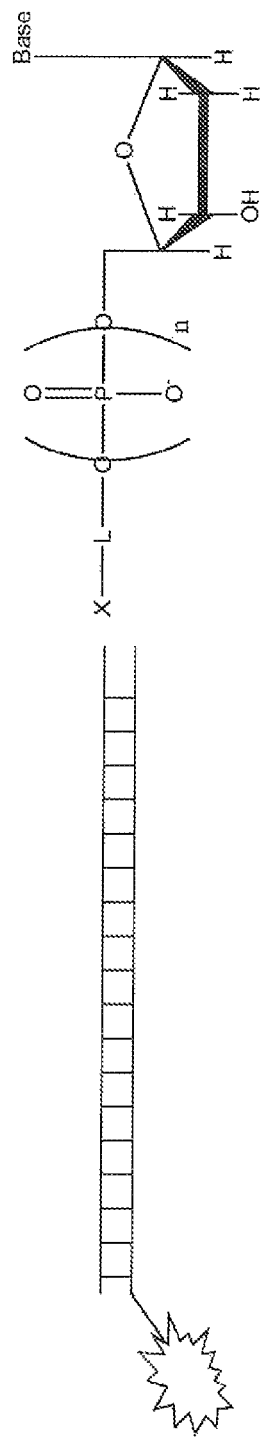
Figure 4C:
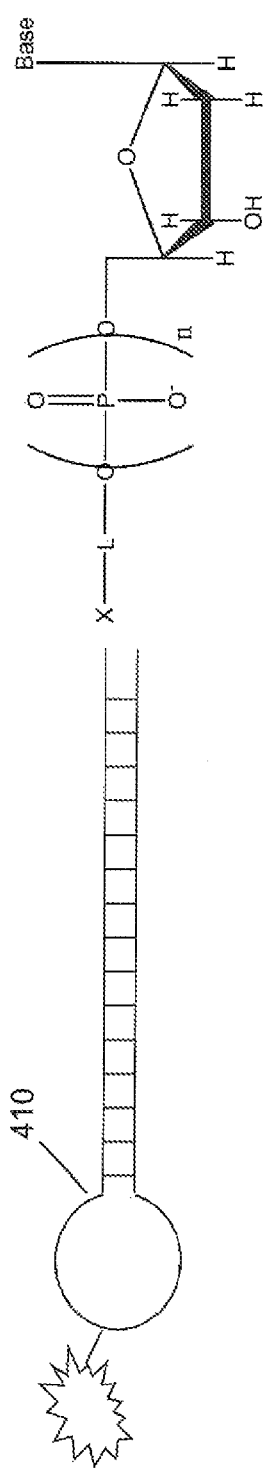

Labeled nucleotide analogs according to this aspect of the invention are schematically illustrated in FIG. 4A, 4B and 4C. In particular, FIG. 4A and B illustrate a nucleic acid linker that employs two distinct but complementary nucleic acid strands 402 and 404 to impart rigidity and length to the linker, so as to provide sufficient functional distance between the reactant component, e.g., nucleotide 406, and the label component, e.g., the fluorophore 408. As shown in FIG. 4A, the label component may be provided directly linked to the reactant portion through the same nucleic acid strand, e.g., oligonucleotide 402. This provides an advantage of maintaining a linked label component regardless of whether the reaction conditions are particularly suited for continued hybridization of the two nucleic acid strands.

Alternatively, the label component may be provided indirectly linked to the reactant portion, as shown in FIG. 4B via the complementary oligonucleotide 404, in order to provide flexibility in coupling of label components to reactant components. In particular, one can assign the particular fluorophore to a particular reactant portion by simply introducing a new labeled nucleic acid that hybridizes with the linker portion of the reactant portion. Additionally, a hybridized or hybridizable label component provides additional flexibility in controlling label association with the reactant that is not available in linkers that involve covalent attachment of the label component to the reactant component. In particular, by adjusting the environmental conditions, one can adjust the level of hybridization between the label component and the reactant component for any of a variety of uses.

In still another aspect, a single nucleic acid strand that includes internally complementary portions, may be employed as the linker, such that the complementary portions can hybridize to form a hairpin loop structure 410, as shown in FIG. 4C. As will be appreciated, coupling of the nucleotide to the oligonucleotide linker may be accomplished through a variety of known linkage chemistries. For example, as shown in FIG. 4, linkage group L may include a variety of groups, including, for example aliphatic linker groups such as the alkyl or other groups previously described herein, such as hexyl linkers. Linkage bond X may include any of a variety of linkages, including thioether linkages, peptide bonds, bifunctional groups, such as malemide-spacer-NHS linkers, to facilitate linkage of the nucleotide to the oligonucleotide linker, and the like. In addition, and as indicated in FIG. 4, the nucleotide may comprise any of a variety of nucleotides or nucleotide analogs, including, for example, nucleoside polyphosphates that include three, four, five or even more phosphates in the phosphate chain, e.g., where n=from 3 to 7. Likewise, the base groups may be similarly modified to achieve a desired application, e.g., substitution of the natural bases with universal bases, or the like.

While preferred embodiments of the invention relate to nucleic acid molecules, including nucleotides, nucleotide analogs, oligonucleotides and polynucleotides, that include the foregoing features, the principles of the invention are equally applicable to a broad range of reactants, labeling groups and their counterpart enzyme systems, such as kinases, phosphatases, and their substrates. For ease of discussion however, the invention is described in terms of fluorescently labeled nucleotides or nucleotide analogs, and their interaction with nucleic acid processing enzymes such as polymerases, including reverse transcriptases, nucleases, ligases, and the like, with DNA polymerases being a particularly preferred enzyme system.

In the context of the foregoing system, the linkers of the invention will typically maintain a functional distance between the reactant nucleotide portion and the label fluorophore portion of at least 1 nm, and in preferred aspects, at least 2 nm or greater.

FIG. 3 schematically illustrates a labeled nucleotide analog employing an oligoproline linker, as described previously. As shown, the reactant portion, e.g., nucleotide, is coupled to the label portion, or dye, such as a fluorophore, via an oligoproline linker that can have a varied length. While the number of proline monomers may be varied depending upon the desired application, such linkers will typically be greater than 1 nm in length, and thus will typically have at least 3 proline monomers (or their equivalents) in the linker (See, e.g., Schuler et al. PNAS 102:2754), e.g., $n \geq 3$, e.g., 3, 4, 5, 6, 10 or greater, to yield linkers having a functional length that is at least 1 nm or greater and preferably at least 2 nm or greater.

III. Applications

As noted previously, the compositions described herein are particularly useful in real-time analytical reactions where one is observing chemical reactions through the illumination of the reaction components. In a particularly preferred aspect, these compositions are useful in real-time analysis of enzymatic reactions using fluorescent or fluorogenic reactants or products, where such fluorescent or fluorogenic reactants or products may detrimentally impact the enzymes they are reacting with. One particularly important example of such a system includes nucleic acid polymerase mediated, template dependent synthesis of nucleic acids, which can be observed using real-time techniques for a variety of desired goals, including in particular, determination of information about the template sequence. A number of methods have been proposed for determination of sequence information using incorporation of fluorescent or fluorogenic nucleotides into the synthesized strand by a DNA or other polymerase, and the compositions of the invention are applicable to these methods. While several of these methods employ iterative steps of nucleotide introduction, washing, optical interrogation, and label removal, preferred uses of these compositions utilize "real-time" determination of incorporation. Such methods are described in detail in, for example, U.S. Pat. Nos. 7,056, 661, 7,052,847, 7,033,764 and 7,056,676, the full disclosures of which are incorporated herein by reference in their entirety for all purposes.

Briefly, such methods observe an immobilized polymerase/template/primer complex as it incorporates labeled nucleotide analogs. Using optical techniques that illuminate small volumes around the complex with excitation radiation, e.g., TIRF methods, optical confinements like Zero Mode Waveguides (ZMWs) (See, U.S. Pat. Nos. 6,917,726, 7,013, 054, 7,181,122, 7,292,742 and 7,170,050 and 7,302,146), and the like, one can identify incorporation events based upon the optical signature of their associated fluorophore, as compared to non incorporated, randomly diffusing labeled nucleotide analogs. By providing each different type of nucleotide with a distinguishable fluorescent label, e.g., having a distinguishable emission spectrum, one can identify each base as it is incorporated, and consequently read out the sequence of the template as the nascent strand is created against it. By utilizing the compositions of the invention, negative impacts of the fluorescent label on the polymerase or other components of the labeled complex (See, e.g., published U.S. Patent Application No. 2007/0161017), can be reduced or eliminated by moving the label portion away from the reactant portion and consequently, the active site of the enzyme, or other sensitive portions of the complex.

IV. Systems

The present invention also employs the nucleotide analog compositions described herein in conjunction with overall analytical systems. Typically, such systems employ a reaction region that is typically disposed in a reaction vessel or well. By way of example, such systems may include a substrate component upon which are immobilized, e.g., a polymerase/template/primer complex, for use in the determination of nucleic acid sequence information of the template, which may be derived from an organism of interest.

Figure 6:
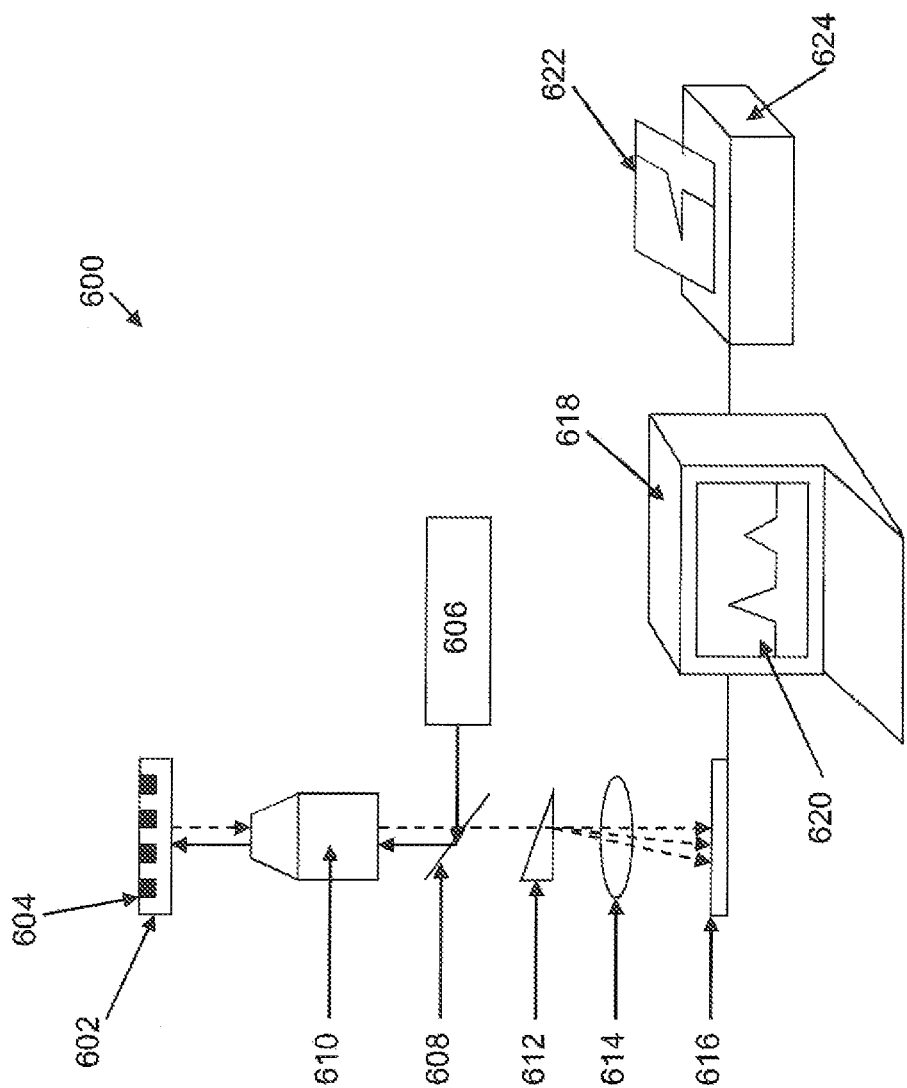
FIG. 6 schematically illustrates one embodiment of a system for use with the compositions and in the methods of the invention.

Because the compositions of the invention are preferably fluorescently labeled, it will be appreciated that the preferred systems of the invention will comprise fluorescence detection functionalities. Examples of such systems include those described in, e.g., Published U.S. Patent Application Nos. 2007/0036511 and 2007/095119 and U.S. patent application Ser. No. 11/901,273 filed Sep. 14, 2007, the full disclosures of which are incorporated herein by reference in their entirety for all purposes. One such system is schematically illustrated in FIG. 6.

As shown, the system 600 includes a substrate 602 that includes a plurality of discrete sources of fluorescent signals, e.g., an array of zero mode waveguides 604. An excitation illumination source, e.g., laser 606, is provided in the system and is positioned to direct excitation radiation at the various fluorescent signal sources. This is typically done by directing excitation radiation at or through appropriate optical components, e.g., dichroic 608 and objective lens 610, that direct the excitation radiation at the substrate 602, and particularly the signal sources 604. Emitted fluorescent signals from the sources 604 are then collected by the optical components, e.g., objective 610, and passed through additional optical elements, e.g., dichroic 608, prism 612 and lens 614, until they are directed to and impinge upon an optical detection system, e.g., detector array 616. The signals are then detected by detector array 616, and the data from that detection is transmitted to an appropriate data processing unit, e.g., computer 618, where the data is subjected to interpretation, analysis, and ultimately presented in a user ready format, e.g., on display 620, or printout 622, from printer 624. As will be appreciated, a variety of modifications may be made to such systems, including, for example, the use of multiplexing components to direct multiple discrete beams at different locations on the substrate, the use of spatial filter components, such as confocal masks, to filter out-of focus components, beam shaping elements to modify the spot configuration incident upon the substrates, and the like (See, e.g., Published U.S. Patent Application Nos. 2007/0036511 and 2007/095119 and U.S. patent application Ser. No. 11/901,273, previously incorporated herein by reference).

V. Kits

The compositions of the invention are optionally provided in kit form, including various components of an overall analysis in combination with instructions for carrying out the desired analysis. In particular, such kits typically include the compositions of the invention, including at least one, but preferably multiple types of labeled nucleotide analogs of the invention, e.g., A, T, G and C analogs. Each of the different types of labeled nucleotide analogs in the kit will typically comprise a distinguishable labeling group, as set forth above. In addition to the analog compositions, the kits will optionally include one or more components of a polymerase complex, including, for example polymerase enzymes, such as any of a number of different types of strand displacing polymerase enzymes. Examples of such polymerases include, e.g., phi29 derived polymerases, and the polymerase enzymes described in, e.g., Published International Patent Application Nos. WO 2007/075987, WO 2007/075873 and WO 2007/076057, the full disclosures of which are incorporated herein by reference in their entirety for all purposes.

Additional reaction components are also optionally included in such kits, such as buffers, salts, universal priming sequences for initiation of synthesis, and the like. In addition, in particularly preferred aspects, the kits of the invention will typically include a reaction substrate that includes reaction regions for carrying out and observing the synthesis reactions for identification of sequence information. Such substrates include, e.g., multi-well micro or nano plates, as well as arrayed substrates, e.g., planar transparent arrays that include discrete reaction regions defined by, e.g., structural, chemical or other means. For example, patterned arrays of complexes may be provided disposed upon planar transparent substrates for observation. Alternatively and preferably, the substrate component comprises an array or arrays of optically confined structures like zero mode waveguides. Examples of arrays of zero mode waveguides are described in, e.g., U.S. Pat. No. 7,170,050, the full disclosure of which is incorporated herein by reference in its entirety for all purposes.

VI. Examples

The use of longer linkers was tested in fluorescently labeled nucleotide analogs to measure its effect on potential negative impacts of illuminated analysis on polymerase enzymes incorporating those analogs. In particular, light-induced damage on surface-immobilized DNA polymerase was determined using an assay described as follows.

Biotin-tagged Phi29 DNA polymerase, complexed in a 1:1 stoichiometry with neutravidin (Pierce), was immobilized on fused silica slides, functionalized with Biotin-polyethyleng-lycol(PEG)-24-silane by 15' incubation at 0 degrees C. in a buffer containing 50 mM Tris acetate, pH 7.5, 75 mM potassium acetate, 0.05% Tween 20 and 5 mM DTT. Unbound polymerase was washed away using the same buffer, and a 72 bp primed, single-stranded, circular DNA template was bound to the polymerase thereafter in a buffer containing 50 mM ACES, pH 7.1, 75 mM potassium acetate, 0.05% Tween 20 and 5 mM DTT. Fluorophore-labeled nucleotides (0.25 uM or Alexa 568 dT6P and Alexa 660 dA6P, with and without an aminohexylaminoheptanoic acid linker), unmodified nucleotides (0.25 uM) and manganese acetate (0.7 mM) were added as applicable to initiate DNA synthesis. The surface-bound polymerase was then exposed to laser illumination by focusing either or both of a 2.1 mW 532 nm laser light, or 2.6 mW of 633 nm laser light (Melles-Griot) an elliptically shaped beam profile (112 um×5 um at 50% intensity drop, using a cylindrical defocusing lens at the entrance of an epifluorescence microscope (Olympus)) to the slide surface (exposure step). After laser exposure, the solution was removed and replaced by an identical reaction solution containing unmodified dATP, dCTP, dGTP, dTTP (10 uM) and the base-labeled nucleotide Alexa Fluor 488-dUTP (1 uM, Invitrogen) (development step). DNA polymerase-mediated incorporation of the latter into DNA yielded fluorescent DNA strands which were imaged by a wide-field epifluorescence microscope, using a Hg arc lamp and standard filters for Alexa Fluor 488 fluorescence detection.

DNA polymerases that remained active after the laser exposure step in the presence of phospholinked nucleotide analogs produce a fluorescence signal while polymerase that were damaged and substantially inactivated were incapable of producing fluorescent DNA in the development step. The signal levels at the center of the elliptical exposure region were quantitated and normalized using an unexposed surface region of the same chip as a control.

Figure 5:
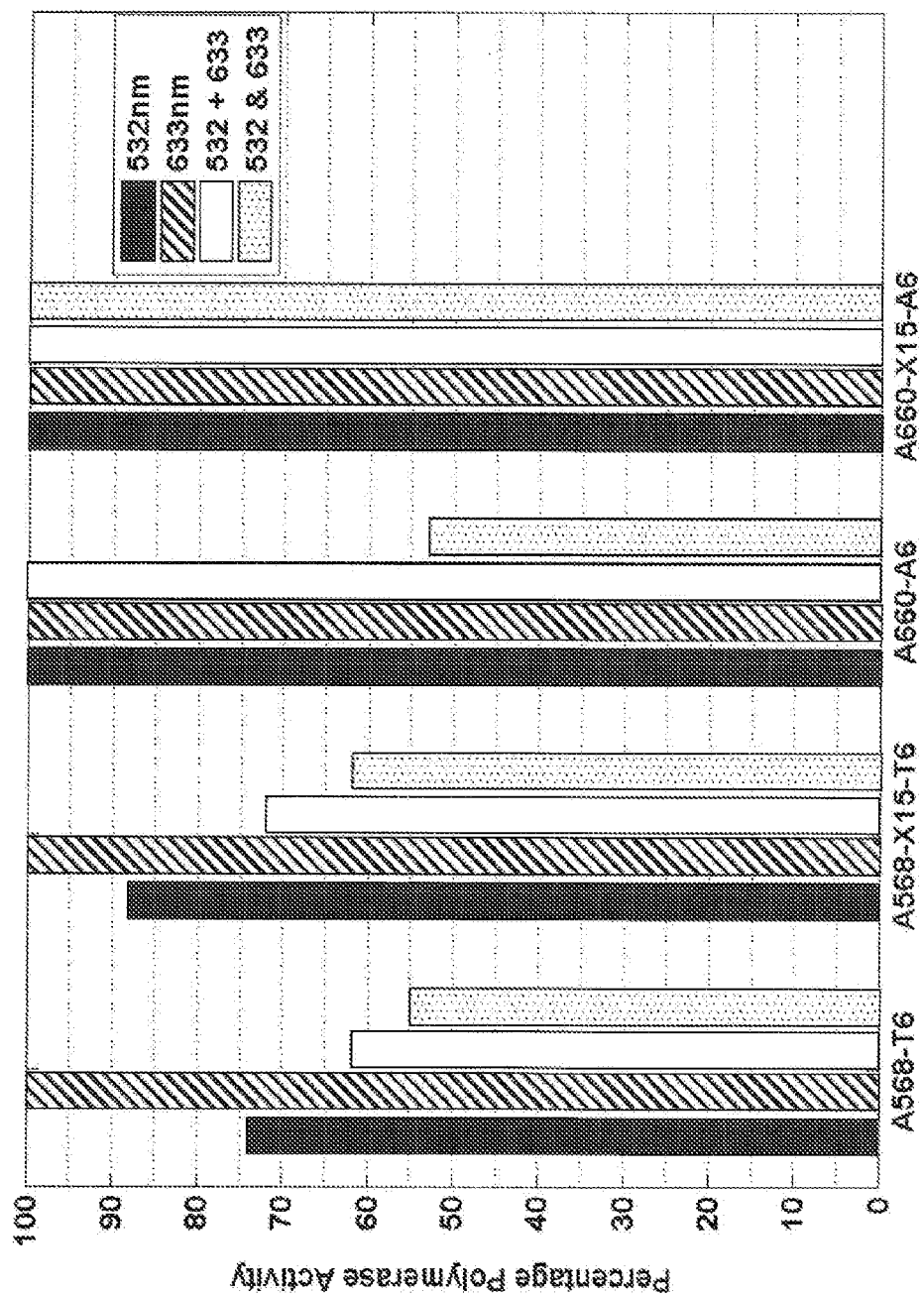
FIG. 5 illustrates improved photostability of polymerase complexes using linkers of the invention.

FIG. 5 illustrates a plot of percentage of polymerase activity following primer extension with either the Alexa 568 or Alexa 660 labeled nucleotide hexaphosphate analogs, and with both a short aminohexyl linker or a longer aminohexyl aminoheptanoic acid linker ("X15") under laser illumination by either the 532 nm laser (first bar from left), the 633 nm laser (second bar) or an iterative (532+633)(third bar) or concurrent (532 & 633) combination of the two (fourth bar).

As can be seen from the plot, the X15 linker provided enhanced survivability of polymerases using both the Alexa 568 and Alexa 660 labeled nucleotides in every case where synthesis was carried out under exposure to at least 532 nm wavelength excitation light. The improvements were even more dramatic when the synthesis involved the use of the Alexa 660 labeled nucleotide under illumination with both the 532 and 633 nm excitation light.

Although described in some detail for purposes of illustration, it will be readily appreciated that a number of variations known or appreciated by those of skill in the art may be practiced within the scope of present invention. All terms used herein are intended to have their ordinary meaning unless an alternative definition is expressly provided or is clear from the context used therein. To the extent any definition is expressly stated in a patent or publication that is incorporated herein by reference, such definition is expressly disclaimed to the extent that it is in conflict with the ordinary meaning of such terms, unless such definition is specifically and expressly incorporated herein, or it is clear from the context that such definition was intended herein. Unless otherwise clear from the context or expressly stated, any concentration values provided herein are generally given in terms of admixture values or percentages without regard to any conversion that occurs upon or following addition of the particular component of the mixture. To the extent not already expressly incorporated herein, all published references and patent documents referred to in this disclosure are incorporated herein by reference in their entirety for all purposes.

What is claimed is:

1. A method of monitoring a nucleic acid synthesis reaction, comprising:

contacting a polymerase/template/primer complex with a fluorescently labeled nucleotide or nucleotide analog having a nucleotide or nucleotide analog component, a fluorescent label component, and a linker component joining the nucleotide or nucleotide analog component to the label component, wherein the linker component is coupled to the nucleotide or nucleotide analog component through a 5'- phosphate group on the nucleotide or nucleotide analog component, and the linker component maintains the label component at a functional distance away from the nucleotide or nucleotide analog component of at least 2 nm; and detecting, a characteristic signal from the fluorescent dye indicative of incorporation of the nucleotide or nucleotide analog into a primer extension reaction.

2. The method of claim 1, wherein the functional distance is at least 5 nm

3. The method of claim 1, wherein the functional distance is at least 10 nm.

4. The method of claim 1, wherein the linker component comprises groups selected from conjugated alkynes, conjugated alkenes, aryl alkynes, aryl amides, polyethylene glycol, oligopeptide, nucleic acids. PNA, and LNA.

5. The method of claim 1, wherein the linker component comprises an oligopeptide.

6. The method of claim 5, wherein the oligopeptide comprises oligoproline.

7. The method of claim 1, wherein the contacting step is carried out under excitation illumination for the label component.

8. The method of claim 1, wherein the detecting step is carried out in real time during a template mediated primer extension reaction.

9. The method of claim 1, wherein the polymerase primer template complex is provided immobilized upon a solid support.

10. The method of claim 9, wherein the solid support comprises a zero mode waveguide, and the complex is immobilized within the zero mode waveguide.

* * * * *